(12) United States Patent
Trabucco

(10) Patent No.: US 6,306,079 B1
(45) Date of Patent: Oct. 23, 2001

(54) MESH PUBOVAGINAL SLING

(76) Inventor: Arnaldo F. Trabucco, 85 Clapham, Manhasset, NY (US) 11030

( * ) Notice: Subject to any disclaimer, the term of this patent is extended or adjusted under 35 U.S.C. 154(b) by 0 days.

(21) Appl. No.: 09/456,007

(22) Filed: Dec. 7, 1999

(51) Int. Cl.$^7$ .................................. A61F 2/00; A61F 5/00
(52) U.S. Cl. ............................................................ 600/30
(58) Field of Search ................... 600/29.31; 602/41–48; 424/423, 426, 428, 430, 443, 444

(56) References Cited

U.S. PATENT DOCUMENTS

| | | |
|---|---|---|
| 3,384,073 | 5/1968 | Winkle, Jr. . |
| 5,007,923 | 4/1991 | Bezwada et al. . |
| 5,013,292 | 5/1991 | Lemay . |
| 5,112,344 | 5/1992 | Petros . |
| 5,256,133 | 10/1993 | Spitz . |
| 5,647,836 | 7/1997 | Blake, III et al. . |
| 5,686,090 | 11/1997 | Schilder et al. . |
| 5,785,640 | 7/1998 | Kresch et al. . |
| 5,792,042 | 8/1998 | Cohen et al. . |
| 5,813,408 | 9/1998 | Benderev et al. . |
| 5,840,011 | 11/1998 | Landgrebe et al. . |
| 5,934,283 | * 8/1999 | Willem et al. ...................... 128/885 |
| 6,010,447 | * 1/2000 | Kardjian .............................. 600/29 |
| 6,039,686 | * 3/2000 | Kovac ................................. 600/30 |

FOREIGN PATENT DOCUMENTS

| | | | |
|---|---|---|---|
| 2787990-A1 | * 12/2000 | (FR) | ...................... 600/30 |
| WO-01/06951-A1 | * 2/2001 | (WO) | ...................... 600/30 |

OTHER PUBLICATIONS

Pubic Bone Suburethral Stabilization Sling for Recurrent Urinary Incontinence Kovac, et al Dec. 1997.

Endoscopic Suspension of Vesical Neck For Urinary Incontinence Schaeffer et al. Urology, Dec. 1985.

* cited by examiner

Primary Examiner—Samuel G. Gilbert
(74) Attorney, Agent, or Firm—Collard & Roe, P.C.

(57) ABSTRACT

A mesh pubovaginal sling comprises two mesh pieces, each having a first mesh portion of polypropylene and a second mesh portion comprising an absorbable material such as poly-dioxanone underlying the first mesh portion. One piece is inserted at the endopelvic fascia and the other at the suprapubic region. The two pieces are then connected via sutures to support prolapsed organs so as to relieve urinary stress incontinence in patients.

13 Claims, 4 Drawing Sheets

MESH PUBOVAGINAL SLING

BACKGROUND OF THE INVENTION

1. Field of the Invention

The invention relates to a surgical implant for treating urinary incontinence. The implant comprises two band-aid-like mesh pieces comprised of absorbable and non-absorbable material. The absorbable material is preferably a monofilament absorbable material that is weaved in a mesh or polyfilament. One suitable material is absorbable poly dioxanone (PDS). The non-absorbable material is preferably polypropylene. Each mesh piece has absorbable material in the middle and non-absorbable material on the ends. One mesh piece is placed in the suprapubic region and the second is placed in the vaginal vault. The two pieces are then tied together via sutures to support the prolapsed organs. The absorbable material dissolves over time.

Nearly 15 to 30 percent of elderly individuals, who are aging continuously, are afflicted with urinary incontinence. Recent estimates show that urinary incontinence affects over 13 million American patients. Approximately 15–20% of women between the ages of 20 and 64 experience urinary incontinence. In many women, urinary incontinence is related to problems of poor pelvic muscle support in the bladder.

Urinary incontinence is defined by the American Urological Association as uncontrolled leakage of urine.

By far the most common type of incontinence is female stress urinary incontinence, accounting for about 75 percent of cases seen by physicians. While female stress urinary incontinence often is a medical disorder seen in older women, it can also occur in younger women, especially those who have had children or with intrinsic sphinteric dysfunction.

2. Description of the Prior Art

U.S. Pat. No. 5,841,011 to Langrebe et al. discloses an implant for suspension of the bladder. The implant is made of a net of polypropylene that is joined with an absorbable material such as polyglactin 910. The implant has a center base and four extending protrusions that are sutured into place. The base then acts as a hammock to support the bladder. The absorbable material dissolves over time, during which connective tissue has been built up to support the bladder on its own.

U.S. Pat. No. 5,647,836 to Blake, III et al. discloses a method and means for treating female urinary incontinence, comprising a pair of anchors having both upper and lower stays connected by sutures. The stays are made of polypropylene or other biologically compatible material.

U.S. Pat. No. 5,013,292 to LeMay discloses a surgical kit for treating urinary incontinence, comprising two implants connected to sutures. The first implant rests on the pubic bone and is preferably made of a titanium alloy. A saddle (shown in FIGS. 3A–3C) is employed to hold the neck of the urethra. The saddle is made of silicone.

U.S. Pat. No. 5,792,042 to Cohen et al. discloses an apparatus for treating incontinence comprising an elongated body having a plug at one end and an external retaining member at the other end. The body is positioned in the urethra with the plug at the interior opening of the urethra and the retaining member at the exterior opening of the urethra. The plug is an inflatable balloon that blocks the flow of urine into the urethra.

U.S. Pat. No. 5,256,133 to Spitz discloses a device for correcting stress urinary incontinence that is implanted to support the urethrovesical junction from the abdominal fascia. The correcting device is implanted via a cannula having a trocar and a push rod.

U.S. Pat. No. 5,112,344 to Petros discloses a method of treating incontinence comprising looping a filament between the wall of the vagina and the rectus abdominis sheath to pull the urethra into the correct position.

U.S. Pat. No. 5,785,640 to Kresch et al. discloses a non-surgical method for treating incontinence comprising an elongated body having anterior support members extending from one end and hemispherical bladder support members extending from the other end.

There are several surgical incontinence devices that utilize hammock-like devices supported by sutures. In addition, the use of a combination of absorbable and non-absorbable materials in such a device is shown in the patent to Landgrebe et al. U.S. Pat. No. 5,813,408 to Benderev et al discloses a surgical treatment of stress urinary incontinence. This procedure is an invasive surgical technique where a probe passes to avoid injuring the bladder and to provide a more accurate and reproducible capture of the pubocervical fascia lateral to the bladder neck and urethra. There is anchor fixation of the suspending sutures to the pubic bone to decrease the risk of suture pull through from above and to decrease post-operative pain. Finally, there is a technique to set a limited tension for the suspending sutures.

U.S. Pat. No. 3,384,073 to W. Van Winkle, Jr. discloses a prosthesis for urinary incontinence. This prosthesis is a woven collagen fabric. The warp yarns may be an extruded collagen multi-filament or monofilament strands. The weft yarns are also collagen multi-filament or monofilament. A series of cuts may be made in the fabric parallel to the warp yarns or the weft yarns. These cuts are in alignment to permit the collagen tape to be laced there through. The collagen prosthesis has the advantage in that it will be absorbed, yet it will provide a wide strength and support for the membranous urethra.

The article "Pubic Bone Suburethral Stabilization Sling for Recurrent Urinary Incontinence", S. Robert Kovac, M.D., and Stephen H. Cruikshank, M.D., Obstetrics & Gynecology 89 No. 4, April 1997 pp. 624–627 discloses a Suburethral sling anchored to the posterior-inferior aspect of the pubic bone with bone screws placed transvaginally. The technique involves placing a Suburethral patch of a synthetic fiber at the junction of the upper one-third and lower two-thirds of the urethra and securing it by titanium bone screws to the posterior-inferior pubis for site-specific urethral support and stabilization of normally positioned continence anatomy.

Finally, "Endoscopic Suspension of Vescial Neck For Urinary Incontinence" by Anthony Schaffer and Thomas Stamey M.D., Urology, Vol. XXIII No. 5, May 1984, pp. 484–494, discloses a surgical procedure for ending urinary incontinence in female patients. Ending urinary incontinence is achieved by elevating the internal vesical neck on both sides with two permanent buttressed nylon loops. The benefits of this procedure include less postoperative morbidity, functional measurements, and anatomic visualization of a restored vesical neck during the procedure, easy access to the surgically difficult pelvis, and simultaneous repair of significant retoceles or substantial cytoceles through the same operative field.

Of most concern in the European community, is that the sling material contains Bovine collagen. Therefore, there is a risk of Mad-Cow disease and the development of human Jacob-Creutzfeld disease being transmitted to the patient, as well as autoimmune collagen diseases in humans due to the inherent antigenicity of collagen.

While the prior art has shown a surgical procedure for ending urinary stress incontinence, the prior art has not shown a surgical implant having two band-aid like mesh pieces comprised of absorbable and non-absorbable material made solely from a non-toxic polymer.

SUMMARY OF THE INVENTION

One object of the invention is to provide a mesh pubovaginal sling for preventing urinary stress incontinence.

Another object of the invention is to provide pubovaginal sling wherein this sling is designed to be inserted and fixed inside a woman without using sutures.

The invention relates to a mesh pubovaginal sling comprising a first piece with an first mesh portion comprising a non-absorbable material such as polypropylene and an second mesh portion comprising an absorbable material. The second mesh portion is preferably made from absorbable poly-dioxanone. In one embodiment of the invention, one piece of the mesh sling is shaped as an octagon. In another embodiment of the invention, the sling is oval or circular. In this embodiment, the first mesh portion may have a hole in the middle. In a third embodiment of the invention, the mesh sling has a first mesh portion that is rectangular or square shaped with an exposed region of the second mesh portion that is square. In another embodiment, the sling comprises two pieces of polypropylene that are sutured together by monofilament PDS as the absorbable portion.

The central band aid mesh consists of a one cm thick absorbable monofilament material such as poly dioxanone (PDS) that is supported by woven monofilament polypropylene. The monofilament polypropylene is woven to allow for proper placement supporting the endopelvic fascia, allowing for fibrosis to support the pelvic contents. After an eight week period, the absorbable portion of this mesh dissolves, at which point all fibroblastic activity that was anticipated is in place and eliminates the risk of any urethral erosion or retention. The results of the implantation studies of PDS II monofilament suture in animals indicated that approximately 70% of its original strength remains two weeks after implementation. At four weeks post implantation, approximately 50% of its original strength is retained, and at six weeks, approximately 25% of the original strength is retained.

The immediate fibroblastic reaction from polypropylene material when inserted under endopelvic fascia acts as a support to the pelvic contents, relieving the pressure off of the urethra while simultaneously resuspending the bladder neck (endopelvic fascia) to its normal anatomical position. Due to the inert properties of polypropylene, infection would not be an issue. The absorbable material under the urethra is degraded by hydrolysis within eight weeks, eliminating the chances for urethral erosion. These advantages also translate into a potential out patient procedure with a reduced hospital stay. This results in a potential cost savings for a health care system, and faster return to normal everyday activities.

The ease of the operation makes this versatile for any urological surgeon to perform as a universal approach to stress urinary incontinence, either type I, type II or type III.

This procedure can be done under local or regional anesthesia and it can be done as an outpatient procedure or overnight stay. There is no drilling of metal into the bones of the patient. Therefore, this prevents the possibility of osteomyelitis. In women with osteoporosis, there is virtually no risk of extrusion of any screws.

The risks of infection are markedly reduced by using all monofilament material. The risk of mesh erosion into the urethra is then eliminated because of the absorbable nature of the mesh in the center.

The option of utilizing a larger vaginal mesh can be determined by the operating surgeon if there is no prolapse components. The use of the anterior mesh releases tension that is traditionally seen with other types of procedures while simultaneously providing a fibroblastic reaction to prevent the sutures from being pulled through the anterial rectal fascia, which has been observed with previous types of repairs. The ease of this operation is universal and can be done by any competent urologist.

The operation consists of a single incision in the subra pubic area. A Stamey needle is utilized to pass behind the space of reitus of the pubic bone after penetrating the anterior rectal fascia at its most inferior location near the pubic bone. One pass is needed for this procedure.

The vaginal mucosal area is then longitudinally incised providing a sharp dissection to accommodate the correct measurements for the placement of the trimmed mesh for correction of the bladder prolapse. Once this dissection is performed, the anterior fascia mesh is reserved for the termination of the procedure. The vaginal mesh is trimmed to the proper dimensions to correct the prolapse of the urinary bladder. To align the absorbable portion along the central portion where the urethra is located, PDS sutures are used to secure the mesh in proper position. Then, nonabsorbable sutures made from a material such as proline are passed through the mesh ends and are then introduced into the eye of the Stamey needle. These sutures are then drawn upward and passed under the endopelvic fascia and pulled through the anterior rectal fascia puncture site. In this case, both sutures are delivered through the same puncture site. Prior to this, the surgeon has accessed the measurements previously taken to correct the prolapsed bladder.

The end of the nonabsorbable sutures is then passed upward to the anterior rectal fascia and guided through the holes of the mesh in two separate locations. The sutures are then tied and secured over the Band-aid mesh on the anterior rectal fascia.

Via the vaginal incision, the mesh is directed with the finger and by pulling the sutures, the edges of the mesh are directed into proper position. Then by tying the sutures under minimal tension and after filling the urinary bladder with fluid by cytoscopy, the endopelvic fascia receives the proper support. Cytoscopy is performed to verify that no bladder perforation has been encountered by the sutures. Prior to tying the sutures, the patient is asked to cough while under spinal or epidural anesthesia, assessing for urinary leakage, wherein the operating surgeon determines the assessment of tension on the sutures. Or, the sutures are tied while a hollow cytoscope sheath is in the urethra and bladder, allowing for an appropriate 15 degree deflection.

After the incontinence operation has been completed surgically, a Bard suprapubic cystomy catheter is inserted into the lower abdominal portion via a puncture, or a Bard Foley catheter is placed in the urinary bladder and the anterior incision is closed with 4.0 monocryl. The vaginal mucosal vertical incision is then closed with PDS sutures.

The potential cost savings for this procedure is substantial since there are no added costs for special types of drapes or drills. In addition, the risk of developing sensitivity to Bovine collagen is nonexistent because the materials used for this sling do not contain animal based materials. Furthermore, the need for endoscopic visualization is reduced by 50 percent. Finally the risk for bladder perforation is reduced dramatically.

BRIEF DESCRIPTION OF THE DRAWINGS

Other objects and features of the present invention will become apparent from the following detailed description considered in connection with the accompanying drawings, which disclose several embodiments of the present invention. It should be understood, however, that the drawings are designed for the purpose of illustration only and not as a definition of the limits of the invention.

DETAILED DESCRIPTION OF THE PREFERRED EMBODIMENT

Figure 1:
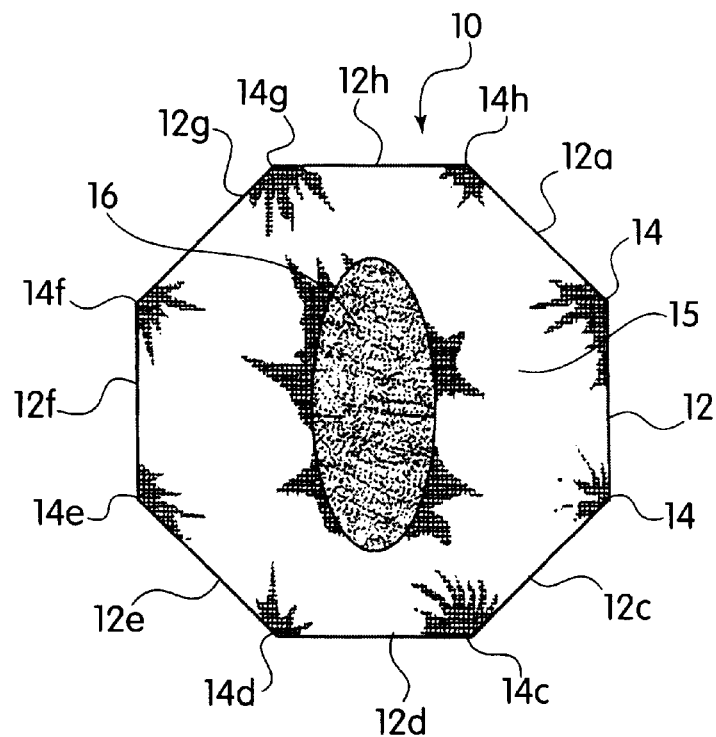
FIG. 1 shows a top view of a first embodiment of one of the mesh pieces of the pubovaginal sling.

Turning to the drawings, FIG. 1 shows a top view of a first embodiment of a pubovaginal sling 10, having a mesh region 16 under a region of monofilament polypropylene 15. First region 15 has a hole therein to expose second region 16. The mesh piece is approximately 5 centimeters high and 1 centimeter wide. The first mesh region 15 is comprised of a nonabsorbable polypropylene material. This first mesh region 15 is shaped as an octagon that has a series of eight sides 12a, 12b, 12c, 12d, 12e, 12f, 12g, 12h and eight corners 14a, 14b, 14c, 14d, 14e, 14f, 14g, and 14h. Ultimately, the use of the anterior mesh releases tension that is traditionally seen with other types of procedures, while at the same time, allowing a fibroblastic reaction in a patient to prevent any sutures from being pulled through the interior rectal region.

Figure 2:
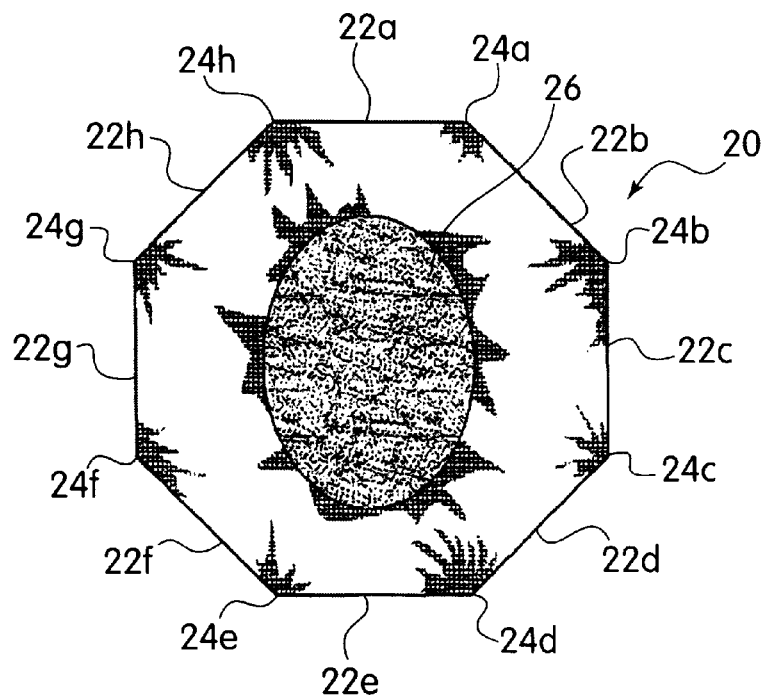
FIG. 2 shows a top view of a second embodiment of one of the mesh pieces of the pubovaginal sling.

FIG. 2 is a second embodiment of the mesh piece wherein the first region 25 is also an octagon that consists of eight sides: 22a, 22b, 22c, 22d, 22e, 22f, 22g, and 22h and eight corners: 24a, 24b, 24c, 24d, 24e, 24f, 24g, and 24h. These first region 25 has a large oval aperture, exposing second region 26 which lies underneath. Similar to the first embodiment, shown in FIG. 1, first region 25 is comprised of polypropylene, while the second region 26 is comprised of PDS. Other materials could also be used, as long as first region 25 is a nonabsorbable material and second region 26 is an absorbable material.

Figure 3:
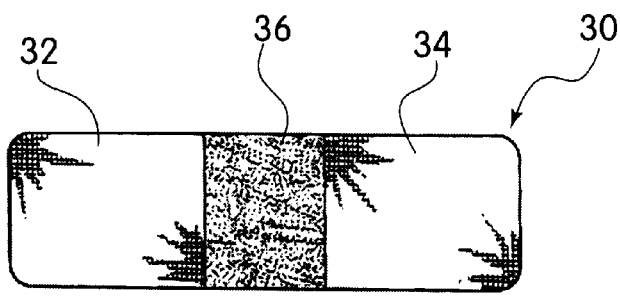
FIG. 3 shows a top view of a third embodiment of one of the mesh pieces of the pubovaginal sling.

FIG. 3 discloses a third embodiment of the invention, showing a piece 30 comprising two regions 32 and 34 and a second region 36, which lies underneath regions 32 and 34. First regions 32 and 34 are substantially rectangular shaped, and second region 36 has a square shaped portion exposed between regions 32 and 34, so that the piece 30 is shaped similar to a band aid. In this case, second region 36 is made of absorbable material such as PDS, while first regions 32 and 34 are made from nonabsorbable material such as polypropylene.

Figure 4:
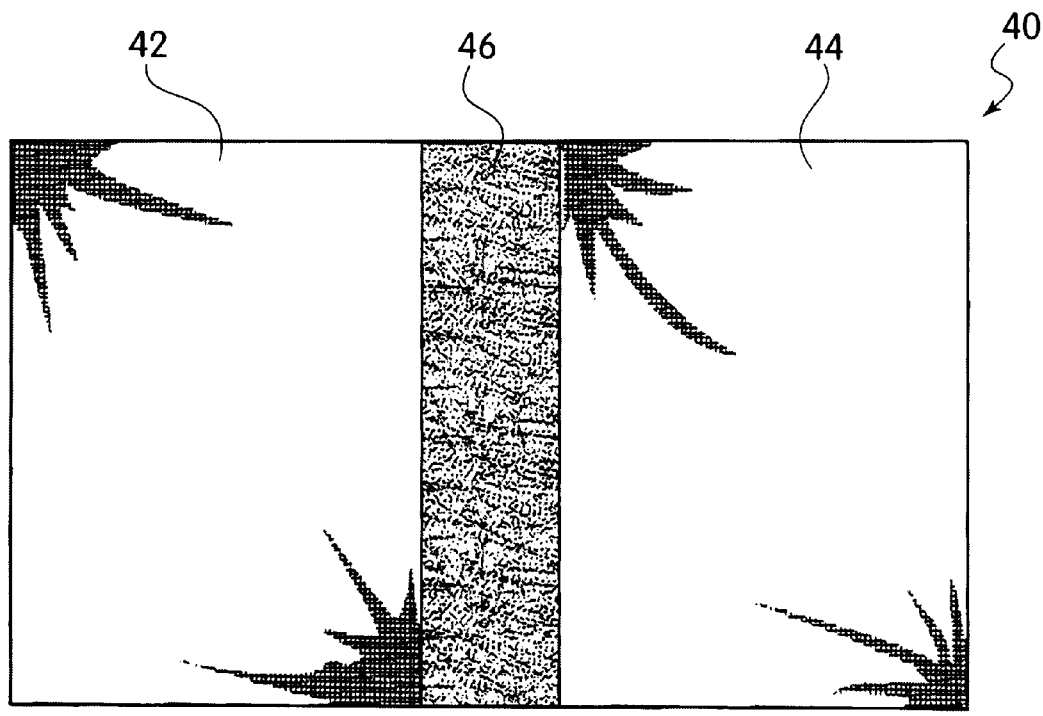
FIG. 4 shows a top view of a fourth embodiment of one of the mesh pieces of the pubovaginal sling.

FIG. 4 discloses a fourth embodiment of the mesh piece of the invention wherein this embodiment shows two first regions 42 and 44 and a second region 46, underlying regions 42 and 44. The two first regions 42 and 44 are substantially rectangular shaped and are made from non absorbable polypropylene material, while the second region 46 exposes a section between regions 42 and 44 that is substantially rectangular shaped and is made from absorbable PDS.

Figure 5:
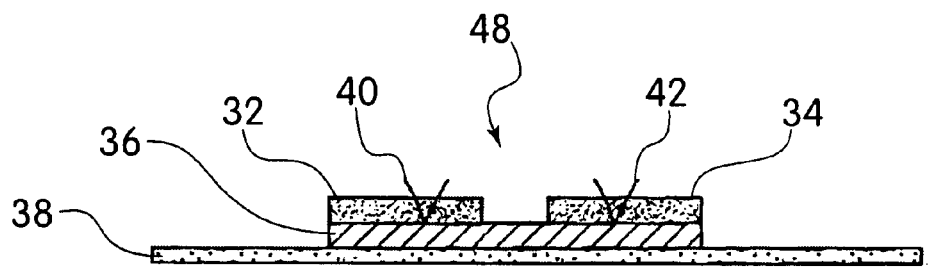
FIG. 5 shows a side view of a one of the mesh pieces according to FIGS. 1–4.

FIG. 5 discloses a side view of any one of the four embodiments of the mesh pieces shown in FIGS. 1–4. In this case, there is an second layer of absorbable material 36 covered by an first layer of spaced apart nonabsorbable material 32 and 34. In the second layer, there are two sections 32 and 34 that are spaced apart from each other. Each of these sections contains sutures 40 and 42. This mesh piece rests upon the interior region 38 inside of a patient.

Figure 6:
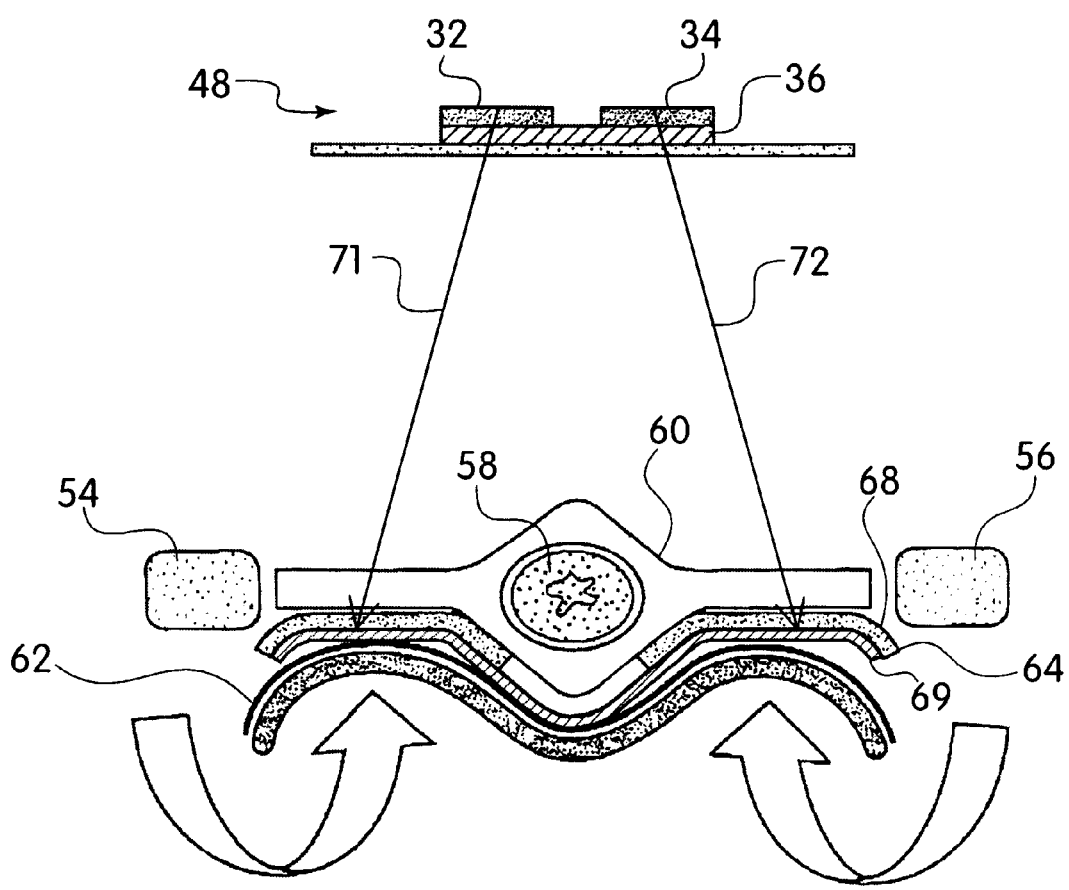
FIG. 6 shows a side view of the sling as inserted into a human body.

FIG. 6 discloses a side view of the mesh pubovaginal sling as inserted into a patient. The inserted mesh piece 64, comprising first nonabsorbable portion 68 and second absorbable portion 69, is inserted just below the periurethral fascia of the urethra. In this case, a series of sutures 50 and 52 are inserted to support mesh piece 64 inside a person's body. Mesh piece 48 is joined with mesh piece 64 via proline sutures 71 and 72. On both a left side of mesh piece 64 and a right side are tendinous arcs 54 and 56. Mesh piece 64 is inserted above vagina 62 so that mesh piece 64 raises the urethra 58 above vagina 62 taking pressure off of vagina 62.

The steps of the operation includes inserting a mesh piece in a suprapubic location. Next, a second band aid mesh is inserted into the vaginal mucosal area where a longitudinal incision is made to place the mesh inside. The vaginal mesh is then trimmed to the proper dimensions to correct the prolapse of the urinary bladder. At the edges of the non-absorbable monofilament polypropylene mesh, sutures are introduced to pass through the anterior rectal fascia and are guided through the holes of the mesh in two separate locations. The sutures are then tied and secured over the band aid mesh on the anterior rectal fascia.

Figure 7:
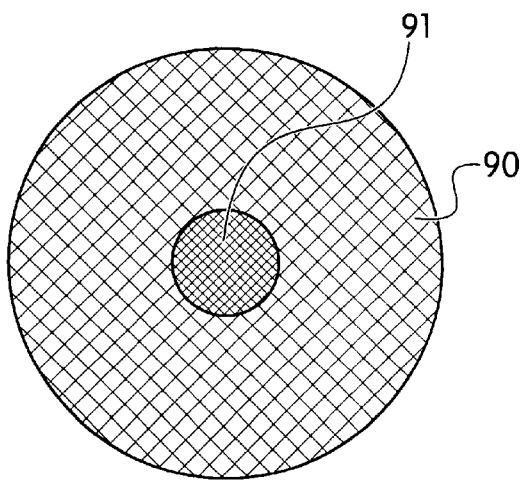
FIG. 7 shows a top view of a fifth embodiment of one of the mesh pieces of the sling according to the invention.
Figure 7A:
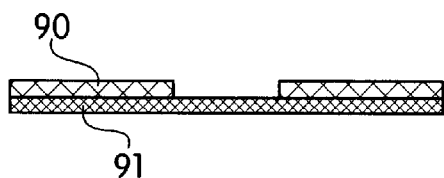
FIG. 7A shows a side view of the embodiment shown in FIG. 7.
Figure 8:
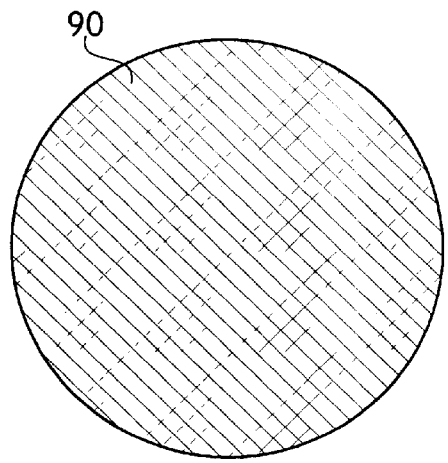
FIG. 8 shows a top view of a sixth embodiment of one of the mesh pieces of the sling according to the invention.
Figure 9:
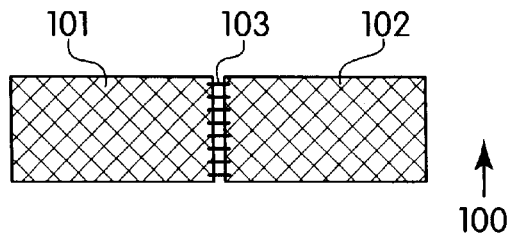
FIG. 9 shows a top view of a seventh embodiment of one of the mesh pieces of the sling according to the invention.

FIGS. 7–9 show further alternative embodiments of the sling according to the invention. FIG. 7 shows the first region 90 made of polypropylene overlying the second region 91 made of absorbable monofilament material such as PDS. Regions 90 and 91 are circular, with a central aperture in region 90 to expose region 91. Alternatively, there could be no aperture, as shown in FIG. 8. Mesh pieces of any shape, such as square, rectangular, oval, etc. could be used in accordance with the invention. FIG. 9 shows another alternative embodiment, in which mesh 100 is made from two pieces of polypropylene 101 and 102 that are held together via absorbable sutures 103.

Accordingly, while several embodiments of the present invention have been shown and described, it is to be understood that many changes and modifications may be made thereunto without departing from the spirit and scope of the invention as defined in the appended claims.

What is claimed is:

1. A mesh pubovaginal sling comprising:
   a first mesh piece comprising:
   i) a first mesh portion comprising a non-absorbable material; and ii) a second mesh portion comprising an absorbable material underneath the first mesh portion; and a second mesh piece attached to said first mesh piece via sutures and said second mesh piece supporting said first mesh piece in the sling.

2. The mesh sling as claimed in claim 1, wherein said second mesh portion is made from absorbable polydioxanone.

3. The mesh sling according to claim 1, wherein said first mesh portion is made of polypropylene.

4. The mesh sling as claimed in claim 1, wherein said first mesh piece is substantially pentagon shaped.

5. The mesh sling as claimed in claim 1, wherein said first mesh piece is shaped substantially oval.

6. The mesh sling as claimed in claim 1, wherein said first mesh piece is shaped substantially rectangular.

7. The mesh sling as claimed in claim 1, wherein the first mesh piece is shaped substantially round.

8. The mesh sling as claimed in claim 7, wherein the first mesh portion has an aperture to expose the second mesh portion.

9. The mesh sling as claimed in claim 1, wherein the second mesh piece further comprises:

i) a first mesh portion comprising a non-absorbable material; and ii) a second mesh portion comprising an absorbable material underneath the first mesh portion.

10. A mesh pubovaginal sling comprising:

a first mesh piece comprising two pieces of non-absorbable material held together via sutures made from an absorbable material; and a second mesh piece attached to said first mesh piece via sutures and said second mesh piece supporting said first mesh piece in the sling.

11. The mesh sling according to claim 10, wherein the first mesh portion is comprised of polypropylene.

12. The mesh sling according to claim 10, wherein the second mesh portion is comprised of absorbable monofilament poly dioxanone.

13. The mesh sling according to claim 10, wherein the second mesh piece comprises two pieces of non-absorbable material held together via sutures made from an absorbable material.

* * * * *